US008804127B2

(12) United States Patent
Shimoyama et al.

(10) Patent No.: US 8,804,127 B2
(45) Date of Patent: Aug. 12, 2014

(54) IMAGE ACQUISITION APPARATUS, IMAGE ACQUISITION SYSTEM, AND METHOD OF CONTROLLING THE SAME

(75) Inventors: Tomohiko Shimoyama, Tokyo (JP); Nobuhito Suehira, Kawasaki (JP); Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 136 days.

(21) Appl. No.: 13/204,953

(22) Filed: Aug. 8, 2011

(65) Prior Publication Data

US 2012/0044499 A1 Feb. 23, 2012

(30) Foreign Application Priority Data

Aug. 19, 2010 (JP) ................................ 2010-184016

(51) Int. Cl.
*G01B 9/02* (2006.01)
*A61B 3/10* (2006.01)
(52) U.S. Cl.
CPC .............. *G01B 9/02* (2013.01); *G01B 2210/52* (2013.01); *A61B 3/102* (2013.01); *G01B 2290/45* (2013.01)
USPC ......................................................... 356/479
(58) Field of Classification Search
CPC .......................... G01B 9/0209; G01B 9/02091
USPC ......... 356/479, 477, 455, 456, 497, 496, 474, 356/932, 450, 453, 491
See application file for complete search history.

(56) References Cited

U.S. PATENT DOCUMENTS

| | | | | |
|---|---|---|---|---|
| 3,643,015 A | * | 2/1972 | Davidovits et al. ............. | 348/79 |
| 5,732,163 A | * | 3/1998 | Brandstetter et al. ......... | 382/296 |
| 5,991,461 A | * | 11/1999 | Schmucker et al. .......... | 382/284 |
| 6,141,462 A | * | 10/2000 | Yoshino et al. ............... | 382/284 |
| 6,198,540 B1 | * | 3/2001 | Ueda et al. ..................... | 356/479 |
| 6,450,641 B2 | * | 9/2002 | D'Souza et al. .............. | 351/212 |
| 6,987,570 B1 | * | 1/2006 | Schmit et al. ................. | 356/511 |
| 7,012,700 B2 | * | 3/2006 | De Groot et al. ............. | 356/512 |
| 7,260,253 B2 | | 8/2007 | Rahn et al. | |
| 7,542,597 B2 | | 6/2009 | Rahn et al. | |
| 7,954,948 B2 | * | 6/2011 | Nozato et al. ................. | 351/206 |
| 2003/0103212 A1 | * | 6/2003 | Westphal et al. ............. | 356/479 |
| 2005/0010108 A1 | | 1/2005 | Rahn et al. | |

(Continued)

FOREIGN PATENT DOCUMENTS

| | | |
|---|---|---|
| JP | 2008-504060 A | 2/2008 |
| JP | 2008-508068 A | 3/2008 |
| JP | 2009-183332 A | 8/2009 |
| JP | 2010-167268 A | 8/2010 |

*Primary Examiner* — Gregory J Toatley
*Assistant Examiner* — Maurice Smith
(74) *Attorney, Agent, or Firm* — Fitzpatrick, Cella, Harper & Scinto

(57) ABSTRACT

An OCT apparatus that photographs with a plurality of measuring beams concurrently, has a mechanism for adjusting the optical path length of a reference beam for each measuring beam. Accordingly, when tomographic images photographed in this manner are displayed side by side, because the depth of photographing varies from one tomographic image to another, it is difficult for an operator to comprehend the positional relation between the photographed images. In displaying tomographic images acquired with a plurality of measuring beams, the display position of each tomographic image is adjusted based on the changed optical path length of a reference beam of the measuring beam used for the image. The tomographic images are thus aligned in height and are presented in a manner that is easy for the operator to comprehend the positional relation between the photographed images.

20 Claims, 10 Drawing Sheets

(56) References Cited

U.S. PATENT DOCUMENTS

| | | | |
|---|---|---|---|
| 2006/0045388 A1* | 3/2006 | Zeineh et al. | 382/312 |
| 2007/0071357 A1 | 3/2007 | Rahn et al. | |
| 2007/0291277 A1* | 12/2007 | Everett et al. | 356/497 |
| 2008/0285043 A1* | 11/2008 | Fercher et al. | 356/451 |
| 2010/0226553 A1 | 9/2010 | Suehira | |
| 2010/0226554 A1 | 9/2010 | Suehira | |
| 2011/0058175 A1 | 3/2011 | Suehira | |
| 2011/0096333 A1 | 4/2011 | Suehira et al. | |
| 2011/0098560 A1 | 4/2011 | Suehira et al. | |
| 2011/0228222 A1 | 9/2011 | Kobayashi | |
| 2011/0299035 A1 | 12/2011 | Suehira | |
| 2012/0075640 A1 | 3/2012 | Sakagawa et al. | |
| 2012/0133950 A1 | 5/2012 | Suehira et al. | |
| 2012/0188510 A1 | 7/2012 | Suehira et al. | |
| 2012/0189184 A1 | 7/2012 | Matsumoto et al. | |

* cited by examiner

IMAGE ACQUISITION APPARATUS, IMAGE ACQUISITION SYSTEM, AND METHOD OF CONTROLLING THE SAME

BACKGROUND OF THE INVENTION

1. Field of the Invention

The present invention relates to an image acquisition apparatus, an image acquisition system, and a method of controlling the same. More particularly, the present invention relates to a tomographic image acquisition apparatus that includes an interference optical system for ophthalmologic examination and other similar uses, a tomographic image acquisition system, and a method of controlling the apparatus.

2. Description of the Related Art

A diversity of ophthalmology equipment that utilizes optical equipment is used today. For instance, anterior segment cameras, fundus cameras, confocal scanning laser ophthalmoscopes (SLOs), and various others are used as optical equipment for observation of the eye. Optical coherence tomography apparatus (hereinafter, referred to as OCT apparatus), in particular, are for taking a tomographic image of a sample at a high resolution, and are becoming indispensable ophthalmology equipment for the diagnosis of retinal diseases.

An OCT apparatus uses an interference system that irradiates a sample with low coherence light and combines light reflected from the sample with a reference beam, to thereby acquire a high-sensitive image of the sample. The OCT apparatus is capable of photographing a tomographic image at a high resolution by scanning a sample with low coherence light. The OCT apparatus can therefore photograph a high-resolution tomographic image of the retina of an examined eye at the fundus, and is widely used in retinal diagnosis.

In the OCT apparatus, by executing a scan in a depth direction (direction Z) of the retina, a called A-scan, and by executing a scan a plurality of times in the direction X (B-scan), a tomographic image of the retina called B-scan image is acquired. With the B-scan image, the internal state of the retina can be observed, unlike an image obtained by the conventional fundus camera or the like. Thus, it is possible to effectively observe lesions inside the retina, in particular, macular degeneration and a macular hole.

An apparatus that takes a plurality of images by shifting the B-scan image in the direction Y to thereby obtain a three-dimensional retinal image is being developed. Obtaining the three-dimensional retinal image provides an advantage in observing the extent of a lesion and each layer inside the retina, particularly, in observing the ganglionic layer of optic nerve, which suffers glaucoma.

Japanese Patent Translation Publication No. 2008-508068 discloses an OCT apparatus that shortens the time required to acquire a three-dimensional retinal image by using a plurality of low coherence light beams and acquiring three-dimensional images of a plurality of areas concurrently.

Japanese Patent Application Laid-Open No. 2009-183332 discloses a so-called single-beam OCT apparatus that photographs three-dimensional images of sections of a scanning area, pieces the three-dimensional images together, and presents the resultant image to the user.

The OCT apparatus that acquires separate images concurrently with the use of a plurality of low coherence light beams requires a mechanism for adjusting the optical path length of the reference beam of each low coherence light beam in order to obtain the optimum image quality for each low coherence light beam. Adjusting the optical path length for each low coherence light beam means that a tomographic image of a different depth is photographed with each low coherence light beam.

Because tomographic images photographed with the respective low coherence light beams are photographs of different depths, users find it difficult to understand the positional relation between the tomographic images that are displayed side by side as they are.

The adjustment of three-dimensional image display positions disclosed in Japanese Patent Application Laid-Open No. 2009-183332 utilizes the similarity between three-dimensional images to be pieced together around the edges. The positioning accordingly takes time.

SUMMARY OF THE INVENTION

The present invention has been made in view of the problems described above, and an object of the present invention is therefore, to display with efficiency, tomographic images that are acquired with the use of a plurality of light beams and have different positions in a depth direction.

In order to solve the problems described above, according to the present invention, there is provided an image acquisition apparatus for acquiring a plurality of tomographic images of an object based on a plurality of combined beams which are obtained by respectively combining a plurality of return beams with a plurality of reference beams, the plurality of return beams being a plurality of measuring beams that return from the object after irradiating the object, the plurality of reference beams respectively corresponding to the plurality of measuring beams. The image acquisition apparatus includes: a display control unit for controlling a display unit to display the plurality of tomographic images which respectively correspond to the plurality of measuring beams; a changing unit for changing optical path lengths of the plurality of reference beams separately; and an image generation unit for generating an image based on the plurality of tomographic images and a result of changes made by the changing unit.

Further, according to the present invention, there is provided an image acquisition system for acquiring a plurality of tomographic images of an object based on a plurality of combined beams which are obtained by respectively combining a plurality of return beams with a plurality of reference beams, the plurality of return beams being a plurality of measuring beams that return from the object after irradiating the object, the plurality of reference beams respectively corresponding to the plurality of measuring beams. The image acquisition system includes: a display control unit for controlling a display unit to display the plurality of tomographic images which respectively correspond to the plurality of measuring beams; a changing unit for changing optical path lengths of the plurality of reference beams separately; and an image generation unit for generating an image based on the plurality of tomographic images and a result of changes made by the changing unit.

Further, according to the present invention, there is provided a method of controlling an image acquisition apparatus for acquiring a plurality of tomographic images of an object based on a plurality of combined beams which are obtained by respectively combining a plurality of return beams with a plurality of reference beams, the plurality of return beams being a plurality of measuring beams that return from the object after irradiating the object, the plurality of reference beams respectively corresponding to the plurality of measuring beams. The method includes: displaying the plurality of tomographic images which respectively correspond to the plurality of measuring beams; and generating an image based on the plurality of tomographic images and a result of changes made to optical path lengths of the plurality of reference beams.

According to the present invention, tomographic images that are acquired with the use of a plurality of light beams and have different positions in the depth direction can be displayed with efficiency.

Further features of the present invention will become apparent from the following description of exemplary embodiments with reference to the attached drawings.

DESCRIPTION OF THE EMBODIMENTS

Embodiments of the present invention are described in detail with reference to the drawings.

First Embodiment

Described as a first embodiment is a multi-beam OCT apparatus that photographs tomographic images (B-scan images) with a plurality of measuring beams and sets the display position of each photographed image based on the optical path length of a reference beam of the measuring beam used for the image.

This OCT apparatus utilizes interference of a measuring beam and a reference beam to create a tomographic image, and is therefore capable of acquiring a tomographic image of an area where the optical path length of the measuring beam and the optical path length of the reference beam are close to each other. An image of an area photographed by the OCT apparatus is clearer when the optical path length of the measuring beam and the optical path length of the reference beam are closer to each other. For that reason, the OCT apparatus adjusts the optical path length of the reference beam for each measuring beam in a manner that makes the depth position optimum for an area measured with the measuring beam.

The thus created difference in optical path length leads to misalignment of tomographic images when the images are displayed, and this embodiment deals with how the multi-beam OCT apparatus corrects the misalignment.

Figure 1:
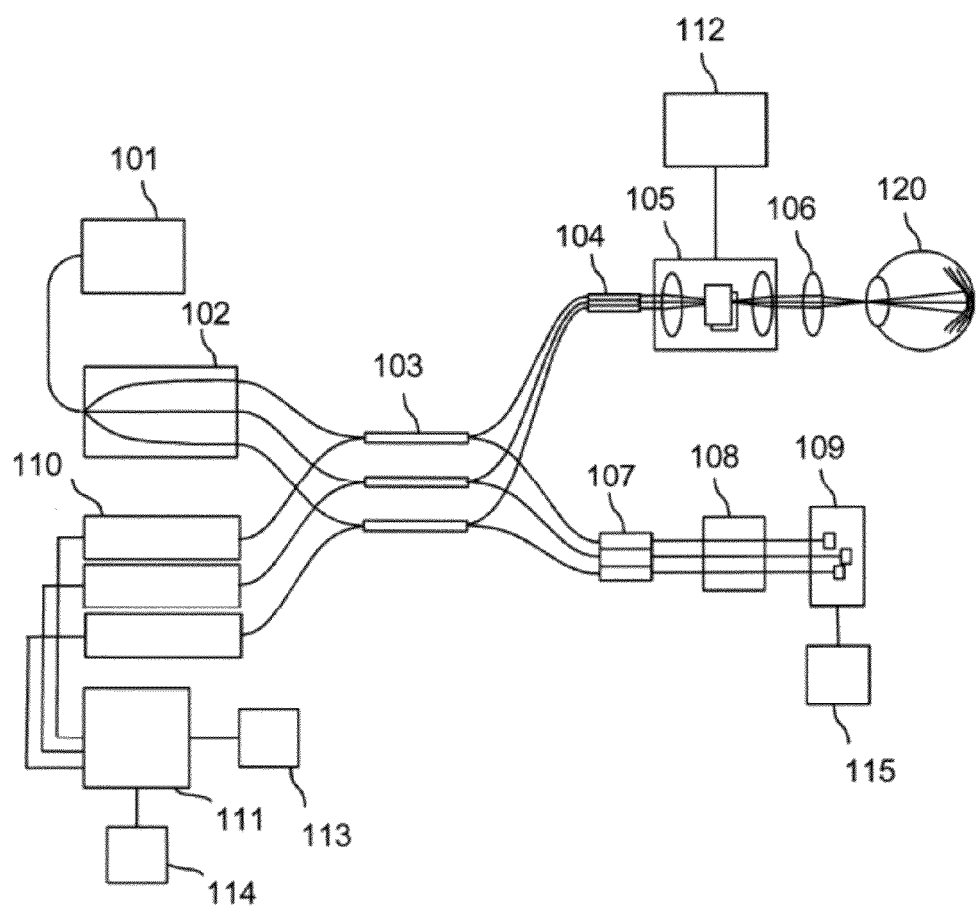
FIG. 1 is a structural diagram of an optical coherence tomography apparatus according to embodiments of the present invention.

FIG. 1 is a structural diagram of the OCT apparatus according to this embodiment.

In FIG. 1, a low coherence light source 101 generates low coherence light. A fiber beam splitter 102 splits the low coherence light that exits the low coherence light source 101 into a plurality of light beams. Fiber couplers 103 further split each of the light beams created by the splitting in the fiber beam splitter 102 into a measuring beam and a reference beam.

The OCT apparatus includes a fiber collimator 104, a scanning optical system 105, an objective lens 106, and a scanning control unit 112. To introduce a plurality of measuring beams into an object, the measuring beams that have exited the fiber collimator 104 are scanned by the scanning optical system 105, which performs beam scanning under control of the scanning control unit 112. After passing through the scanning optical system 105, those measuring beams irradiate areas of an object 120 (object to be measured for examination) via the objective lens 106, which constitutes an irradiation optical system. The interval between fibers of the fiber collimator 104 and the relation between components of the scanning optical system 105 are set such that the measuring beams on the object 120 are spaced at a specific interval. The measuring beams are reflected or scattered by the object 120, which is an examination object, and the resultant return beams travel through the same optical systems to return to the fiber couplers 103.

The areas of the object 120 scanned with the respective measuring beams are described with reference to FIG. 2.

Figure 2:
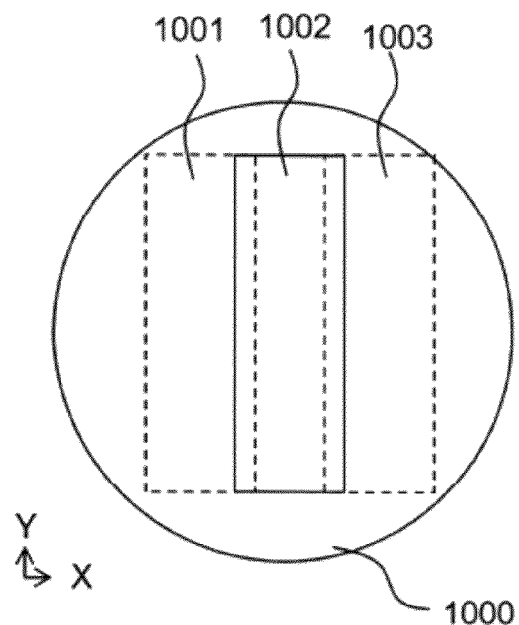
FIG. 2 is a diagram illustrating scanning areas of respective measuring beams in a first embodiment.

FIG. 2 is a diagram illustrating areas that are scanned with the respective measuring beams when the object 120 is a fundus. In FIG. 2, which is a monitor image described later, a fundus 1000 has areas 1001 (the left hand-side area enclosed by a dashed line), 1002 (the area enclosed by a solid line), and 1003 (the right hand-side area enclosed by a dashed line) to be scanned (photographed) with separate measuring beams. In this embodiment, scanning areas are set such that three measuring beams divide the object 120 into three sections in a main scanning direction (direction X) to photograph a three-dimensional image of each area. Specifically, the fiber collimator 104, the scanning optical system 105, and other components are arranged in a manner that makes the area 1001 and the area 1002 partially overlap with each other in the main scanning direction, and the area 1002 and the area 1003 partially overlap with each other in the main scanning direction.

Returning to FIG. 1, the OCT apparatus further includes a fiber collimator 107, a dispersion compensating glass 108, a reference mirror unit 109, and a reference mirror control unit 115. Reference beams exit the fiber collimator 107, pass through the dispersion compensating glass 108, reflected by the reference mirror unit 109, and return to the fiber couplers 103. The reference beams are designed to pass through the dispersion compensating glass 108 in order to match the amount of chromatic dispersion of the reference beams with the amount of chromatic dispersion of the measuring beams.

Figure 3:
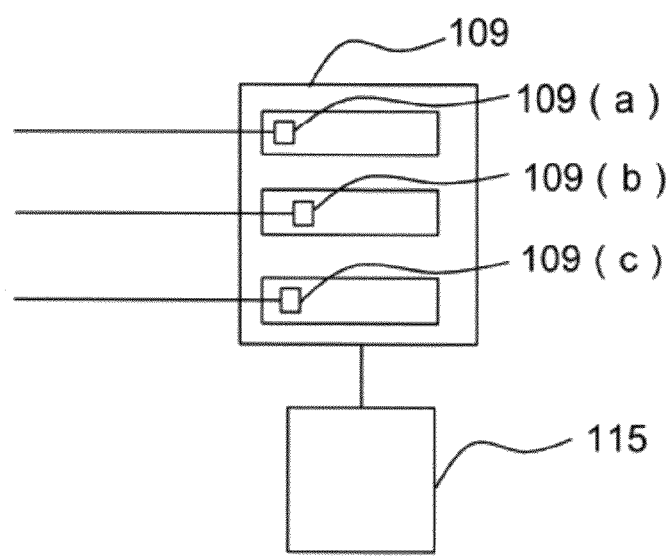
FIG. 3 is a diagram illustrating the structure of a reference mirror unit.

The reference mirror unit 109 is described with reference to FIG. 3. The reference mirror unit 109 contains therein a plurality of mirrors mounted to individual stages (in this embodiment, three reference mirrors 109(a), 109(b), and 109(c)). The stages are driven and controlled by the reference mirror control unit 115 to adjust the optical path lengths of a plurality of reference beams separately. In this embodiment, the positions of the reference mirrors relative to one another in the case where the reference beams travel through reference paths that have the same length are stored in the reference mirror control unit 115 in advance to be used in calculating the deviations of the reference mirrors. The reference mirror unit 109 and the reference mirror control unit 115 constitute an adjustment unit which adjusts the optical path length of each reference beam, in other words, the length of each reference beam path. The adjustment unit changes the optical path lengths of a plurality of reference beams and may be called as, for example, a changing unit.

Returning to FIG. 1, the OCT apparatus further includes detection units 110, an information processing unit 111, a display unit 113, and an operation unit 114. The measuring beams reflected/scattered by the object 120 and returned to the fiber couplers 103 and the reference beams reflected by the reference mirror unit 109 and returned to the fiber couplers 103 are combined by the fiber couplers 103 to create combined beams. Based on the combined beams, interference signals are generated.

The interference signals generated by the combining in the fiber couplers 103 are detected by the detection units 110 as interference signals that correspond respectively to the measuring beams. The detection units 110 have the same structure as in known SD-OCT, and are constituted by diffraction gratings, line sensors, or the like.

The interference signals detected by the detection units 110 are transformed by the information processing unit 111 through a Fourier transform with the wave numbers of the coherent beams, to thereby obtain tomographic images of the areas of the object 120. The detection units 110 and the information processing unit 111 function as an image forming unit, which causes a reference beam and a measuring beam to interfere with each other to generate, for each of a plurality of beams irradiating the examination object, a tomographic image that corresponds to the beam. The display unit 113 functions as a display unit capable of displaying tomographic images that are photographed with the plurality of beams in the present invention.

The OCT apparatus also includes a scanning laser ophthalmoscope (SLO) (not shown), or a photographic system (not shown) for photographing two-dimensional fundus images, in order to monitor the image-taking positions.

In the case where a macula is set as the center of an area to be photographed, for example, a luminescent spot (not shown) called a fixation lamp is placed along an optical axis, and a subject person is asked to fix his/her sight on the fixation lamp. The macula, which is the center of the field of vision, is thus placed along the optical axis and the fundus can be scanned while centering the macula. By adjusting the position of the fixation lamp, a desired area can be photographed.

In the OCT apparatus described above, one line of A-scan (direction Z) data is obtained for each measuring beam through measurement performed without moving the scanning optical system 105. Each time photographing of one A-scan line is completed, the scanning control unit 112 drives the scanning optical system 105 in a manner that moves the current measuring beam by an amount corresponding to the unit of resolution in the direction X in preparation for the photographing of the next line. By continuing photographing in this manner, B-scan images are obtained. The scanning optical system 105 is further driven in a manner that moves the current measuring beam by an amount corresponding to the unit of resolution in a direction Y, and continuing photographing in this manner produces three-dimensional images.

Next, processing of displaying tomographic images that is executed by the information processing unit 111 according to this embodiment is described with reference to a flow chart of FIG. 4. The information processing unit 111, as described later, also functions as a display control unit which performs display control operations, such as causing a display unit to display a plurality of tomographic images on the same display screen. The display control unit causes the display unit to display a plurality of tomographic images that respectively correspond to a plurality of measuring beams.

The information processing unit 111 first acquires (photographs) tomographic images with three beams (S100). How the tomographic images are photographed is described. To photograph tomographic images, the reference mirror positions are adjusted first. The information processing unit 111 controls the display unit 113 to display tomographic images photographed with three measuring beams in separate windows, along with an adjustment tool for adjusting the optical path lengths of three reference beams (for example, a slide bar which is moved with a mouse following the cursor). Looking at the tomographic images displayed in the separate windows, an operator operates the adjustment tool via the operation unit 114 in a manner that aligns the tomographic images optimally, to thereby issue an instruction to change the position of the corresponding reference mirror. Based on the instruction, the information processing unit 111 controls the reference mirror control unit 115 to adjust the positions of the reference mirrors 109(a), 109(b), and 109(c) separately. An instruction to end the reference mirror adjustment is given from the operation unit 114, and then tomographic images used for diagnosis are photographed. The information processing unit 111 thus adjusts and changes the display positions of the respective tomographic images in accordance with operations made by the operator to the operation unit 114.

Figure 5:
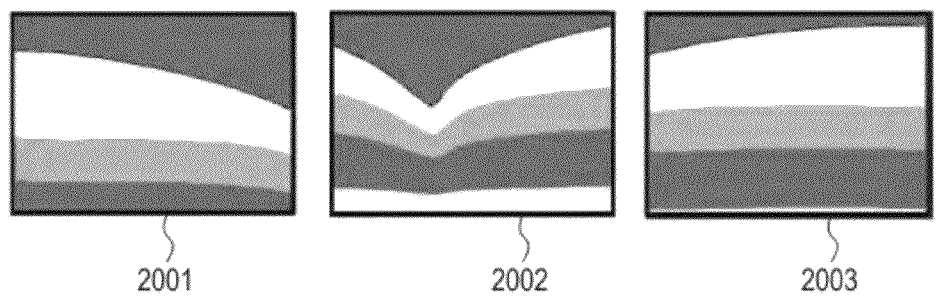
FIG. 5 is a collection of tomographic images photographed with the respective measuring beams.

FIG. 5 illustrates tomographic images 2001, 2002, and 2003 acquired with three measuring beams after the reference mirror positions are adjusted.

Figure 4:
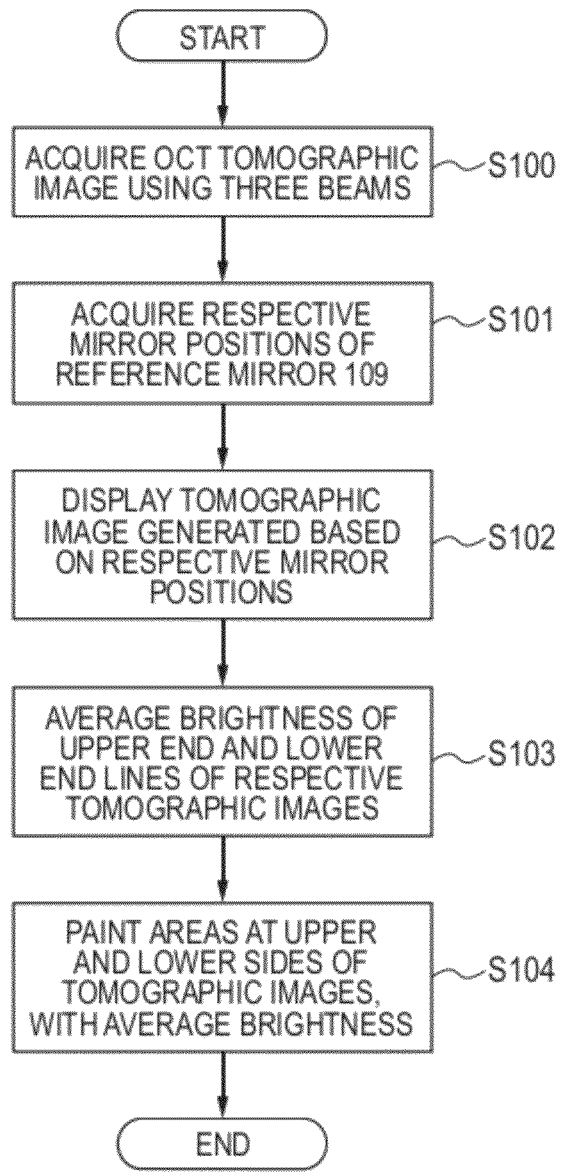
FIG. 4 is a flow chart illustrating processing that is executed in an information processing unit according to the first embodiment.

In Step S101 of FIG. 4, the information processing unit 111 acquires from the reference mirror control unit 115 information about positions that the reference mirrors 109(a), 109(b), and 109(c) are in when the tomographic images of FIG. 5 are photographed. The positions of the reference mirrors respectively correspond to depths at which the tomographic images acquired in Step S100 are photographed. Based on the acquired information about the positions of the reference mirrors, the information processing unit 111 calculates the amount of misalignment between the tomographic images (the amount of offset in the depth direction). In other words, the information processing unit 111 adjusts the display positions of the tomographic images based on the adjusted optical path lengths of the reference beams which have been adjusted separately by the reference mirror control unit 115.

Next, in Step S102, the information processing unit 111 shifts the display positions of the tomographic images based on the calculated amount of misalignment to generate a composite tomographic image in which the shifted images partially overlap with one another, and displays the composite tomographic image on the display unit 113. The information processing unit 111 of the present invention functions, in this case, as an image generation unit, which generates a composite tomographic image of the object from a plurality of tomographic images based on the result of changes made by the changing unit, namely, the calculated amount of misalignment.

The display positions of the respective tomographic images in the direction X are set in advance in accordance with the distance between adjacent measuring beams. The display positions of the respective tomographic images in the direction Y are shifted based on the positions of the respective reference mirrors. Each displayed tomographic image is shifted by an amount that corresponds to a difference of the reference mirror position of the tomographic image from a reference position, which is the smallest of the reference mirror positions or the position of the central reference beam. In other words, the information processing unit 111 shifts the positions of the tomographic images in the depth direction at the time of generation, which are calculated based on the changed positions of the reference mirrors, to thereby position the tomographic images in the depth direction and generate an image. This includes, in terms of operation, correcting the position of each of the plurality of tomographic images in the depth direction in accordance with the amount of change made by the changing unit to the initial display position of the tomographic image.

Figure 6:
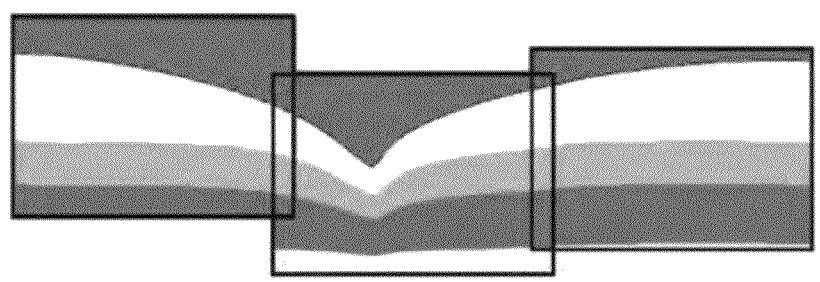
FIG. 6 is a composite tomographic image in which misalignment has been corrected.

FIG. 6 illustrates a composite tomographic image displayed on the display unit 113 in which tomographic images corrected for misalignment are partially overlapped with one another.

As illustrated in FIG. 6, a plurality of tomographic images having different positions in the depth direction can be pieced together in a favorable manner with a tomographic image display apparatus and control method according to the present invention through the operations described above. Tomographic images that do not make the operator aware of their differences in position in the depth direction can thus be generated in a short period of time.

Next, in Step S103, the average brightness of one line at the upper end and the average brightness of one line at the lower end are obtained for each tomographic image. In Step S104, areas above and below each tomographic image where there are no images are painted solidly at the calculated average brightnesses. This operation is executed by the information processing unit 111.

How a part of the composite tomographic image is painted solidly is described with reference to FIG. 7 and FIGS. 8A to 8C.

Figure 7:
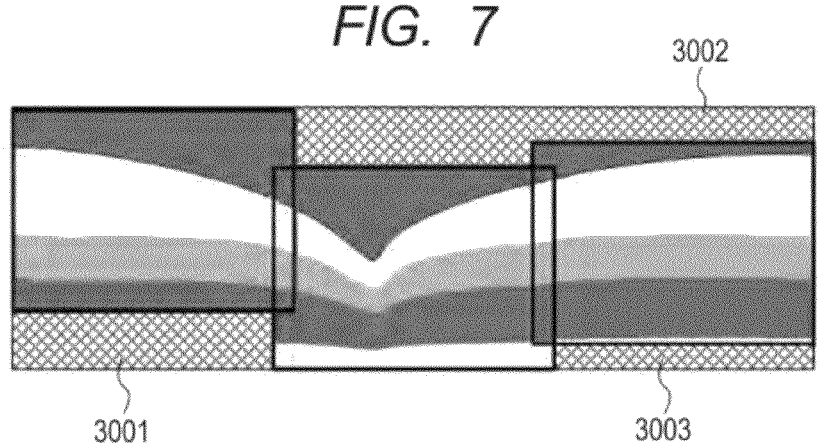
FIG. 7 is a diagram illustrating how a part of the composite tomographic image is painted solidly.
Figure 8A:
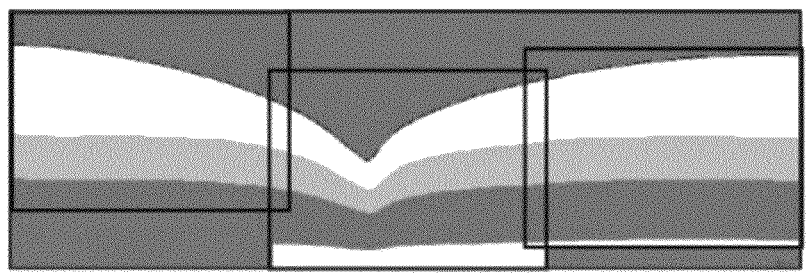
FIGS. 8A, 8B and 8C are diagrams illustrating how a part of the composite tomographic image is painted solidly.

In FIG. 7, of areas inside the smallest rectangle that circumscribes the tomographic images, areas 3001, 3002, and 3003 contain no images. Each of the no-image areas above or below one of the tomographic images is painted solidly at the relevant average brightness calculated in Step S103 for the tomographic image. The resultant tomographic image displayed on the display unit 113 is illustrated in FIG. 8A. In this example, each tomographic image is displayed along with a frame that indicates the outer edge of the display area of the tomographic image.

With the tomographic image display apparatus and control method according to the present invention, a plurality of tomographic images having different positions in the depth direction is displayed in a manner that is easy for the operator to comprehend the positional relation between the tomographic images, and a composite tomographic image in which the constituent tomographic images are smoothly pieced together is provided at the same time.

Figure 8B:
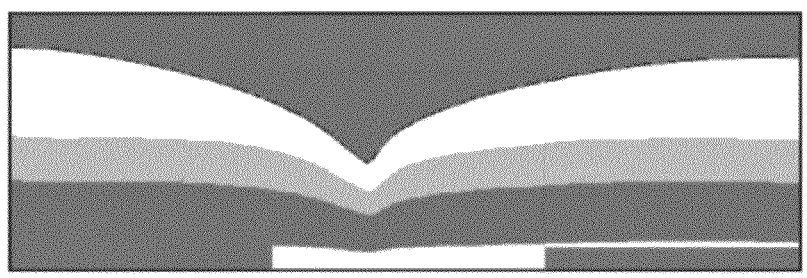
Figure 8C:
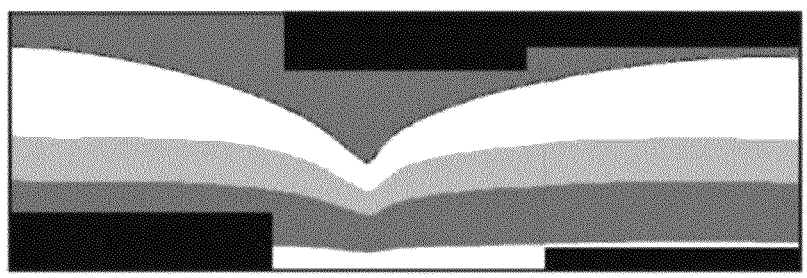

The frame of each tomographic image may not be displayed as in FIG. 8B, and a switch from one selected image to another may be displayed visually. As in FIG. 8C, non-image areas may be displayed the same way low brightness areas are displayed, specifically, may be displayed black. In this case, the information processing unit 111 includes a portion that functions as a painting unit, which paints a no-image area above or below an image solidly at a brightness suited to the image, or in a specific color.

Fundus tomographic images photographed with a plurality of beams, and accordingly having different depths, are aligned (in height) through the procedures described above. The positional relation between the tomographic images is thus presented in a manner that is easy for an operator to comprehend.

In addition, areas having no images that are created as a result of piecing tomographic images together are painted solidly at a brightness suited to the nearby tomographic images, thereby relieving a feeling of strangeness that may be felt by the operator. Displaying non-image areas in black, conversely, makes it clear that there are no images in these areas.

While this embodiment discusses a three-beam OCT apparatus, the present invention is not limited thereto and is applicable to an OCT apparatus that uses an arbitrary number of measuring beams.

The heights of tomographic images, which are adjusted based on the adjusted optical path lengths of reference beams in this embodiment, may be adjusted further finely based on the similarity between overlapped areas of the tomographic images.

In this embodiment, areas scanned with separate measuring beams are partially overlapped. However, the present invention is not limited thereto and the scanning areas may be in close proximity to one another instead of overlapping.

This embodiment takes as an example of the adjustment unit of the present invention a structure constituted by the reference mirror unit 109 and the reference mirror control unit 115. However, the present invention is not limited to this structure and this structure may be replaced with various other structures that can change the optical path length.

Second Embodiment

A second embodiment describes a multi-beam OCT apparatus that photographs three-dimensional scan images with a plurality of measuring beams, and changes the display position of each of the scan images based on the adjusted optical path length of a reference beam of the measuring beam used for the image.

Figure 9:
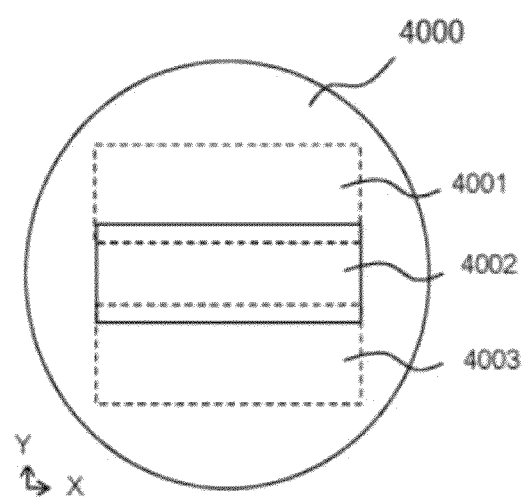
FIG. 9 is a diagram illustrating scanning areas of respective measuring beams in a second embodiment.

In this embodiment, as illustrated in FIG. 9, an object is divided into three areas in a sub-scanning direction (direction Y) to photograph three-dimensional images with three beams. In FIG. 9, which is a monitor image, a fundus 4000 has areas 4001, 4002, and 4003 to be photographed as three-dimensional images with the three beams.

Figure 10A:
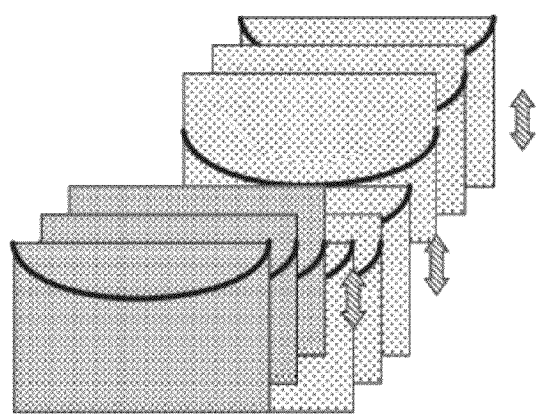
FIGS. 10A and 10B are diagrams illustrating display according to the second embodiment.
Figure 10B:
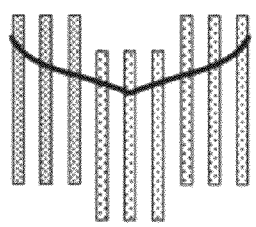

The OCT apparatus displays a plurality of photographed three-dimensional images next to one another with their display positions shifted from one another, in a manner that is easy for the operator to comprehend the positional relation between the three-dimensional images. The height adjustment of the three-dimensional images (adjustment in the direction Z) is based on the adjusted optical path lengths of reference beams (FIGS. 10A and 10B).

In this embodiment, the display position of each three-dimensional image is adjusted based on the adjusted optical path length of a reference beam of a measuring beam used for the image, to thereby shorten the processing time (calculation time).

A comparison between three-dimensional images generally requires a large amount of calculation, and it is difficult to piece together, based on similarity, two three-dimensional images that are significantly misaligned as a result of intentionally varying the optical path lengths for the images. Adjusting the display positions based on the adjusted optical path lengths therefore provides a great advantage.

The structure of the second embodiment is basically the same as that of the first embodiment. The description given here is therefore about differences from the first embodiment. The second embodiment differs from the first embodiment in that the arrangement of the fiber collimator 104 and the relation between components of the scanning optical system 105 are set differently in order to make scanning areas partially overlap with one another in the sub-scanning direction, that a three-dimensional image of the retina is acquired by scanning in the direction Y each time B-scan is completed, and how the information processing unit 111 executes processing of displaying three-dimensional images.

Details of acquiring three-dimensional images are as described above. Described here is how the information processing unit 111 executes processing of displaying three-dimensional images.

Figure 11A:
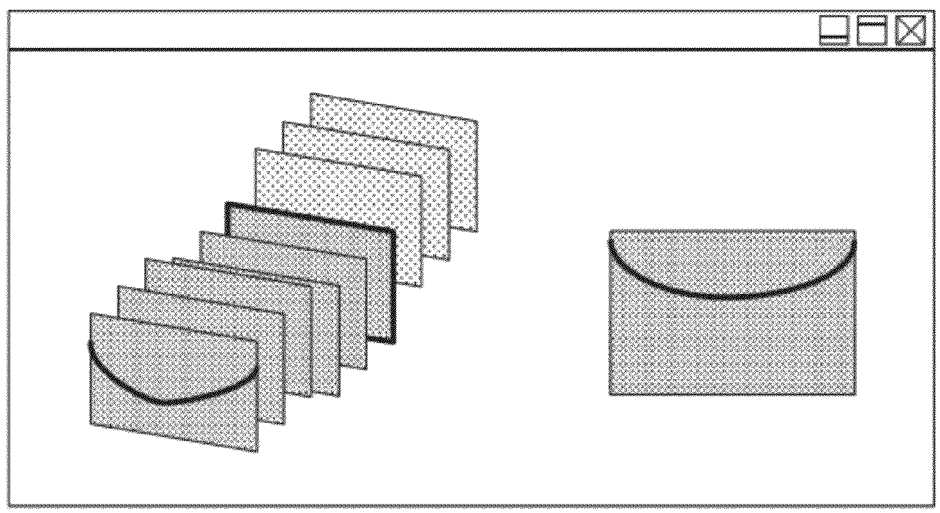
FIGS. 11A and 11B are diagrams illustrating display according to the second embodiment.
Figure 11B:
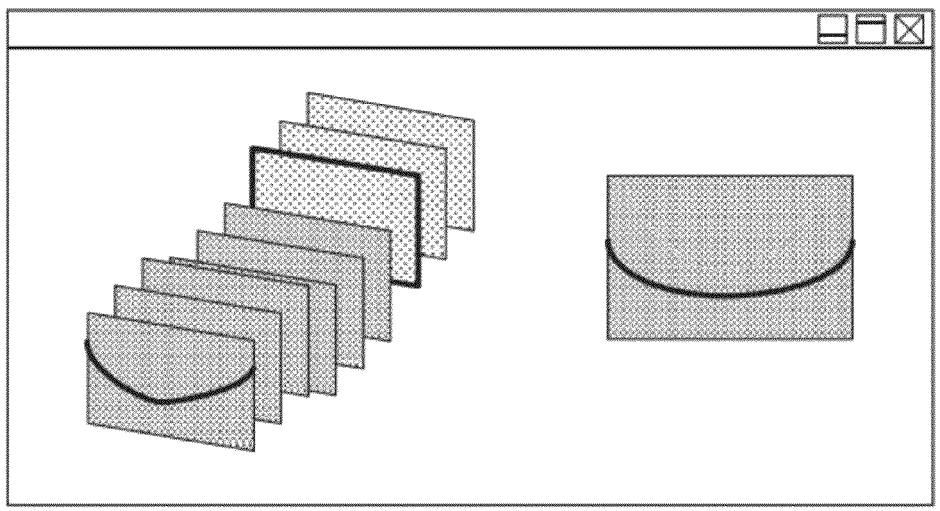

FIGS. 11A and 11B illustrate three-dimensional image-display windows that are displayed on the display unit 113 under control of the information processing unit 111.

In each three-dimensional image display window, a total image of three-dimensional images is displayed on the left hand side, and an operator uses the operation unit 114 to point and select with the cursor an area that the operator wishes to see. For instance, the operator selects an image that he/she wishes to see by moving a bold-line frame in the window, and a two-dimensional tomographic image of one of the three-dimensional images is displayed on the right hand side.

The two-dimensional tomographic image is displayed after its display position is adjusted based on the adjusted optical path length of a reference beam of a measuring beam used for the image, which is adjusted with the shortest optical path length as the reference.

A display example of two-dimensional tomographic images acquired with different beams is described with reference to FIGS. 11A and 11B. In FIGS. 11A and 11B, adjacent two-dimensional tomographic images photographed with different beams are displayed.

Because the two beams have different adjusted optical path lengths of reference beams, the displayed two-dimensional tomographic images differ from each other in display position (the position in the top-bottom direction within the window).

Although the two-dimensional tomographic images are displayed at different display positions in FIGS. 11A and 11B, the display positions of retinal images photographed as tomographic images do not move within the three-dimensional image display windows. Accordingly, even when the operator selects different areas from the total image of three-dimensional images in succession, the display positions of retinal images do not change and the positional relation between retinal images remains easy for the operator to comprehend.

Figure 12:
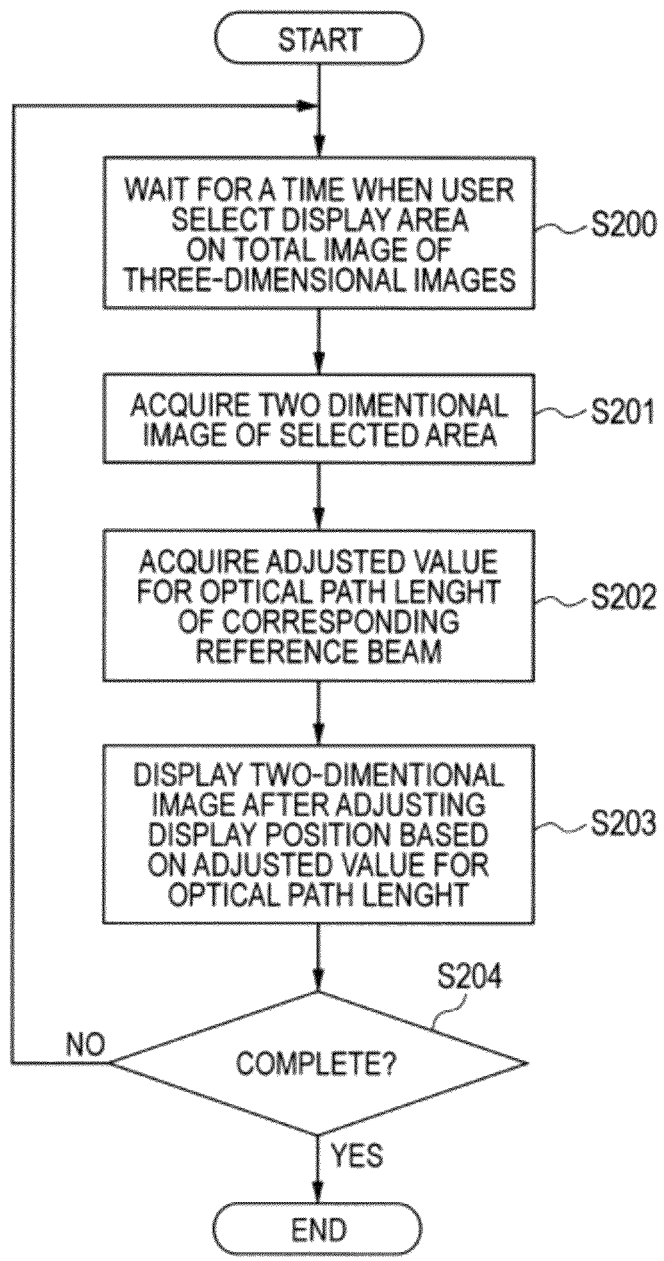
FIG. 12 is a flow chart illustrating processing that is executed in an information processing unit according to the second embodiment.

FIG. 12 is a flow chart of a control program executed by the information processing unit 111 according to the second embodiment.

The control program is of event-driven type, and waits until the operator selects a display area from the total image of three-dimensional images in the three-dimensional image display window (S200).

When the operator selects a display area, a two-dimensional tomographic image of the selected area and the adjusted optical path length of a reference beam of the corresponding measuring beam are acquired (S201 and S202).

The acquired two-dimensional tomographic image is displayed after the display position of the image is adjusted based on the adjusted optical path length (S203).

If the processing is not complete, the control program returns to Step S200 (S204).

Through the procedures described above, the display position of each of three-dimensional scan images photographed with a plurality of measuring beam can be adjusted based on the adjusted optical path length of a reference beam of a measuring beam used for the image.

By adjusting the display positions of three-dimensional scan images, tomographic images of a fundus can be displayed at constant positions on the display screen, and are thus presented in a manner that is easy for the operator to comprehend the positions of the tomographic images.

Third Embodiment

A third embodiment describes a multi-beam OCT apparatus that photographs B-scan images with a plurality of measuring beams, and changes the display position of each of the B-scan images based on an instruction from an operator.

In this embodiment, the display positions of tomographic images, which are changed based on the adjusted optical path lengths of reference beams in the first embodiment, are changed based on an instruction from the operator.

The third embodiment also changes the color of areas where tomographic images partially overlap with one another in a manner that reflects the degree of similarity between the overlapped areas. Overlapped areas that have high similarity are displayed in the usual black-and-white, whereas overlapped areas that have low similarity are displayed in a color different from the color of its surroundings, for example, in red color.

Figure 13A:
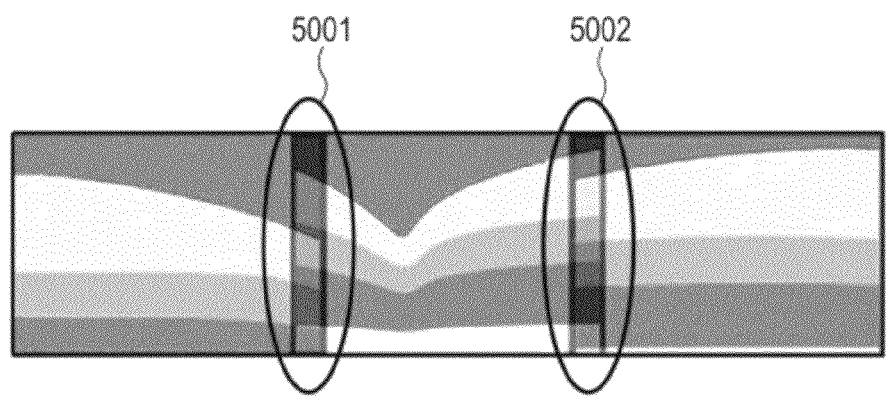
FIGS. 13A and 13B are diagrams illustrating display according to a third embodiment.
Figure 13B:
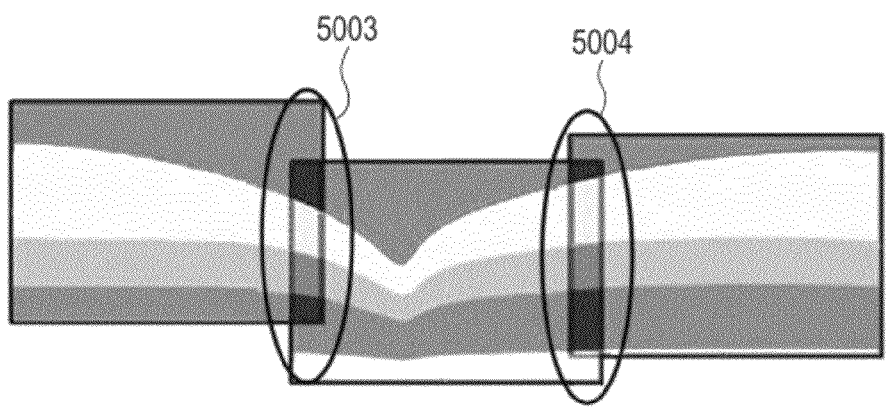

A display example of tomographic images according to this embodiment is illustrated in FIGS. 13A and 13B.

FIG. 13A illustrates how tomographic images look before the operator changes the display positions of the tomographic images. Areas 5001 and 5002 in FIG. 13A contain significant differences between the overlapped images, and the overlapped areas are therefore displayed in red.

FIG. 13B illustrates how the tomographic images look after the operator changes the display positions of the tomographic images. Areas 5003 and 5004 in FIG. 13B contain only small differences between the overlapped images, and are therefore displayed in black-and-white.

The structure of the third embodiment is basically the same as that of the first embodiment. The description given here is therefore about differences from the first embodiment.

The third embodiment differs from the first embodiment in how the information processing unit 111 executes processing of displaying tomographic images.

Figure 14:
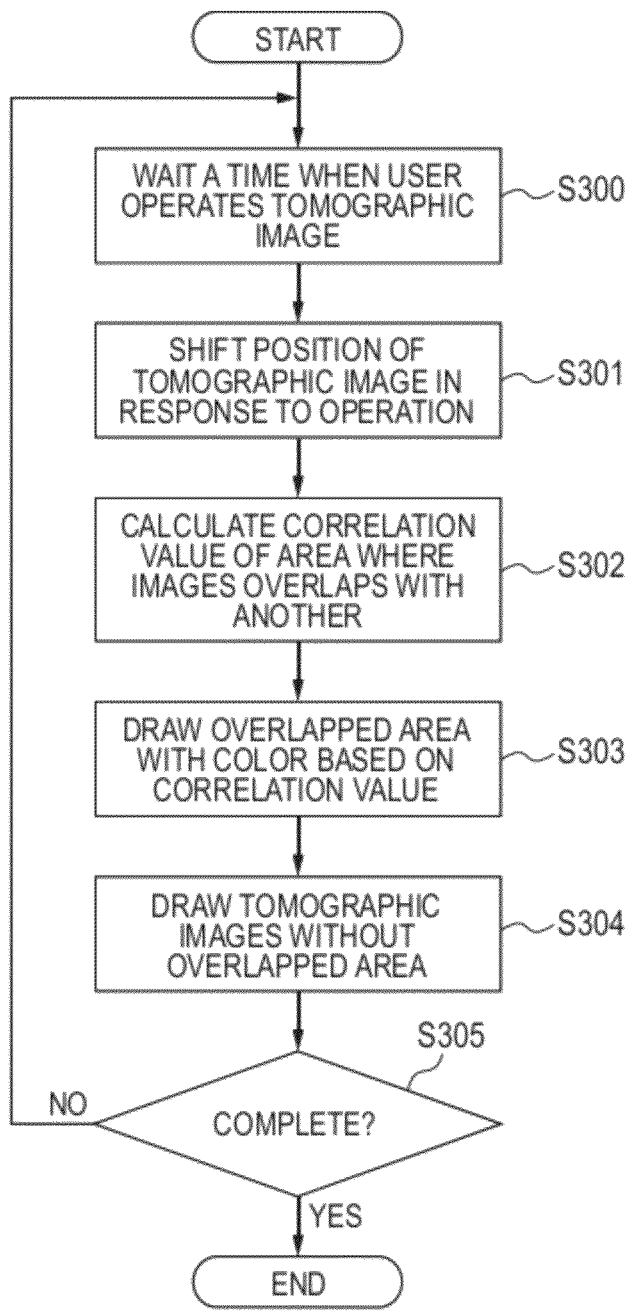
FIG. 14 is a flow chart illustrating processing that is executed in an information processing unit according to the third embodiment.

FIG. 14 is a flow chart of a method of displaying tomographic images.

The information processing unit 111 uses an event-driven type control program, and the control program waits until the operator operates tomographic images (S300).

The display positions of the tomographic images are changed internally in response to the operator's operation (S301). However, actual images are not drawn yet at this point.

Next, areas where the tomographic images partially overlap with one another are calculated and correlation values of the overlapped areas are calculated (S302). The correlation values can be calculated by various methods and, in this embodiment, the mean square error is employed.

The images in the overlapped areas are drawn in colors based on the correlation values (S303). In this embodiment, overlapped areas having high similarity are drawn in black-and-white and overlapped areas having low similarity are drawn in red. The overlapped areas of two images are drawn as translucent images in order to enable the operator to compare the two.

Areas where images do not overlap with one another are then drawn in black-and-white (S304).

If the processing is not complete, the control program returns to Step S300 (S305).

Through the procedures described above, the display positions of tomographic images photographed with a plurality of beams can be changed based on an instruction from the operator. The color of areas where tomographic images partially overlap with one another is changed in a manner that reflects the degree of similarity between the overlapped areas. In short, the processing unit in this embodiment displays areas where a plurality of tomographic images overlap with one another in a color that is different from the normal display color and that reflects the correlation between the overlapped areas of the tomographic images. This enables the operator to easily find out display positions to be adjusted and the amount of adjustment required.

By adjusting the display positions of tomographic images, the tomographic images are presented in a manner that is easy for an operator to comprehend the positional relation between the tomographic images. The tomographic images can therefore be easily positioned with one another.

Another Embodiment

Further, the present invention may be realized by executing the following processing as well. Specifically, in the processing, software (program) for implementing the functions of the embodiments described above is supplied to a system or an apparatus via a network or various kinds of storage media, such as non-transitory tangible media readable by a computer and storing programs executable by a computer, and a computer of the system or the apparatus (or CPU, MPU, etc.) reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-184016, filed Aug. 19, 2010, which is hereby incorporated by reference herein in its entirety.

What is claimed is:

1. An imaging apparatus comprising:
an irradiating unit configured to irradiate different areas of an object in an intersecting direction to an optical axis of an optical path with a plurality of measuring beams;
an acquiring unit configured to acquire a plurality of tomographic images of the different areas based on a plurality of combined beams which are obtained by combining a plurality of return beams from the object irradiated by the plurality of measuring beams and a plurality of reference beams corresponding to the plurality of measuring beams;
a display control unit configured to control a display unit to display the plurality of tomographic images;
a changing unit configured to change optical path lengths of the plurality of reference beams separately; and
an image generation unit configured to generate a new tomographic image by correcting a displacement between the plurality of tomographic images along an image direction corresponding to a depth direction of the object, wherein the displacement corresponds to at least a difference between the changed optical path lengths.

2. An imaging apparatus according to claim 1, wherein the image generation unit generates the new tomographic image by connecting the plurality of tomographic images, each of whose displacement is corrected, and wherein the display control unit causes the display unit to display the new tomographic image.

3. An imaging apparatus according to claim 1, further comprising a scanning unit configured to scan the plurality of measuring beams over the object in a main scanning direction,
wherein the plurality of measuring beams scan over scanning areas that are separated from one another in the main scanning direction.

4. An imaging apparatus according to claim 1, wherein the image generation unit changes display positions of the plurality of tomographic images on the display unit in accordance with the changed optical path lengths which are changed by the changing unit.

5. An imaging apparatus according to claim 1, wherein the image generation unit displays on the display unit the plurality of tomographic images along with frames that represent outer edges of display areas of the plurality of tomographic images.

6. An imaging apparatus according to claim 1, wherein the image generation unit changes display positions of the plurality of tomographic images on the display unit in accordance with an operation made by an operator.

7. An imaging apparatus according to claim 1, wherein the image generation unit comprises a unit configured to solidly paint areas containing no images which are generated as a result of the changes made to display positions of the plurality of tomographic images on the display unit, at brightnesses suited to the plurality of tomographic images.

8. An imaging apparatus according to claim 1, wherein the image generation unit displays, on the display unit, areas where the plurality of tomographic images overlap with one another in a color that reflects a degree of correlation between the overlapped tomographic images.

9. An image acquisition system comprising:
an irradiating unit configured to irradiate different areas of an object in an intersecting direction to an optical axis of an optical path with a plurality of measuring beams;
an acquiring unit configured to acquire a plurality of tomographic images of the different areas based on a plurality of combined beams which are obtained by combining a plurality of return beams from the object irradiated by the plurality of measuring beams and a plurality of reference beams corresponding to the plurality of measuring beams;
a display control unit configured to control a display unit to display the plurality of tomographic images;
a changing unit configured to change optical path lengths of the plurality of reference beams separately; and
an image generation unit configured to generate a new tomographic image by correcting a displacement between the plurality of tomographic images along an image direction corresponding to a depth direction of the object, wherein the displacement corresponds to at least a difference between the changed optical path lengths.

10. A method of controlling an imaging apparatus including an irradiating unit configured to irradiate different areas of an object in an intersecting direction to an optical axis of an optical path with a plurality of measuring beams, the method comprising:

acquiring a plurality of tomographic images of the different areas based on a plurality of combined beams which are obtained by combining a plurality of return beams from the object irradiated by the plurality of measuring beams and a plurality of reference beams corresponding to the plurality of measuring beams;

controlling a display unit to display the plurality of tomographic images;

changing optical path lengths of the plurality of reference beams separately; and generating a new tomographic image by correcting a displacement in between the plurality of tomographic images along an image direction corresponding to a depth direction of the object, wherein the displacement corresponds to a difference between the changed optical path lengths.

11. A non-transitory tangible medium having recorded thereon a program that controls a computer to execute each step of the control method according to claim 10.

12. An information processing apparatus comprising:

an acquiring unit configured to acquire a plurality of tomographic images of different areas of an object in an intersecting direction to an optical axis of an optical path based on a plurality of combined beams which are obtained by combining a plurality of return beams from the object irradiated by a plurality of measuring beams and a plurality of the reference beams corresponding to the plurality of measuring beams;

a display control unit configured to control a display unit to display the plurality of tomographic images; and an image generation unit configured to generate a new tomographic image by correcting a displacement in between the plurality of tomographic images along an image direction corresponding to a depth direction of the object, wherein the displacement corresponds to at least differences between the optical path lengths of the plurality of reference beams.

13. An image processing apparatus according to claim 12, wherein the image generation unit generates the new tomographic image by connecting the plurality of tomographic images each of which displacement is corrected, and the display control unit causes the display unit to display the new tomographic image.

14. A method of controlling an image processing apparatus, comprising the steps of:

acquiring a plurality of tomographic images of different areas of an object in an intersecting direction to an optical axis of an optical path based on a plurality of combined beams which are obtained by combining a plurality of return beams from the object irradiated by a plurality of measuring beams and a plurality of the reference beams corresponding to the plurality of measuring beams;

controlling a display unit to display the plurality of tomographic images; and generating a new tomographic image by correcting a displacement between the plurality of tomographic images along an image direction corresponding to a depth direction of the object, wherein the displacement corresponds to at least a difference between the optical path lengths of the plurality of reference beams.

15. A method of controlling an image processing apparatus according to claim 14, wherein the new tomographic image is generated by connecting the plurality of tomographic images, each of whose displacement is corrected, and the display unit is controlled to display the new tomographic image.

16. A non-transitory tangible medium having recorded thereon a program that controls a computer to execute each step of the control method according to claim 14.

17. An imaging apparatus according to claim 1, further comprising:

an objective lens commonly provided on optical paths of the plurality of the measuring beams; and a scanning optical system commonly provided on optical paths of the plurality of the measuring beams.

18. An imaging apparatus for acquiring a plurality of tomographic images of an object based on a plurality of combined beams which are obtained by respectively combining a plurality of return beams with a plurality of reference beams, the plurality of return beams being a plurality of measuring beams that return from the object after irradiating the object, the plurality of reference beams respectively corresponding to the plurality of measuring beams, the imaging apparatus comprising:

a display control unit configured to control a display unit to display the plurality of tomographic images;

a changing unit configured to change optical path lengths of the plurality of reference beams separately; and an image generation unit configured to generate a new tomographic image by correcting a displacement between the plurality of tomographic images along an image direction corresponding to a depth direction of the object, the displacement being directed to a difference between the changed optical path lengths, respectively, in the depth direction.

19. A method of controlling an imaging apparatus for acquiring a plurality of tomographic images of an object based on a plurality of combined beams which are obtained by respectively combining a plurality of return beams with a plurality of reference beams, the plurality of return beams being a plurality of measuring beams that return from the object after irradiating the object, the plurality of reference beams respectively corresponding to the plurality of measuring beams, the method comprising:

controlling a display unit to display the plurality of tomographic images;

changing optical path lengths of the plurality of reference beams separately; and generating a new tomographic image by correcting a displacement between the plurality of tomographic images along an image direction corresponding to a depth direction of the object, the displacement being directed to a difference between the changed optical path lengths, respectively, in the depth direction.

20. A non-transitory tangible medium having recorded thereon a program that controls a computer to execute each step of the control method according to claim 19.

* * * * *